(12) United States Patent
Lafond et al.

(10) Patent No.: US 12,213,505 B2
(45) Date of Patent: Feb. 4, 2025

(54) COMPOSITION FOR PROMOTING RESTFUL SLEEP AND METHODS OF MAKING AND USING THE SAME

(71) Applicant: Celesta Company LLC, Galesburg, MI (US)

(72) Inventors: David Wilfred Lafond, Galesburg, MI (US); Christine Lynn O'Neil, Jupiter, FL (US); Jean-Pierre Montmayeur, Atlanta, GA (US)

(73) Assignee: Healthy Ingredient Solutions, LLC, Jupiter, FL (US)

( * ) Notice: Subject to any disclaimer, the term of this patent is extended or adjusted under 35 U.S.C. 154(b) by 0 days.

(21) Appl. No.: 17/855,430

(22) Filed: Jun. 30, 2022

(65) Prior Publication Data
US 2023/0039674 A1  Feb. 9, 2023

Related U.S. Application Data

(60) Provisional application No. 63/218,457, filed on Jul. 5, 2021.

(51) Int. Cl.

| | | |
|---|---|---|
| *A23L 33/105* | (2016.01) | |
| *A23L 2/52* | (2006.01) | |
| *A61K 9/00* | (2006.01) | |
| *A61K 31/05* | (2006.01) | |
| *A61K 31/122* | (2006.01) | |
| *A61K 31/194* | (2006.01) | |
| *A61K 31/198* | (2006.01) | |
| *A61K 31/352* | (2006.01) | |
| *A61K 31/4045* | (2006.01) | |
| *A61K 31/4415* | (2006.01) | |
| *A61K 31/7004* | (2006.01) | |
| *A61K 31/7016* | (2006.01) | |
| *A61K 33/06* | (2006.01) | |

(52) U.S. Cl.
CPC ........... *A23L 33/105* (2016.08); *A23L 2/52* (2013.01); *A61K 9/0095* (2013.01); *A61K 31/05* (2013.01); *A61K 31/122* (2013.01); *A61K 31/194* (2013.01); *A61K 31/198* (2013.01); *A61K 31/352* (2013.01); *A61K 31/4045* (2013.01); *A61K 31/4415* (2013.01); *A61K 31/7004* (2013.01); *A61K 31/7016* (2013.01); *A61K 33/06* (2013.01)

(58) Field of Classification Search
CPC ......... A23L 33/105; A23L 2/52; A61K 31/05; A61K 31/122; A61K 31/194; A61K 31/198; A61K 31/352; A61K 31/4045; A61K 31/4415; A61K 31/7004; A61K 31/7016; A61K 33/06
USPC .......................................................... 514/25
See application file for complete search history.

(56) References Cited

U.S. PATENT DOCUMENTS

| | | |
|---|---|---|
| 5,449,683 A | 9/1995 | Wurtman |
| 6,391,346 B1 | 5/2002 | Newmark et al. |
| 6,399,116 B1 | 6/2002 | Xiu |
| 6,703,412 B1 | 3/2004 | Rosenthal |
| 7,445,864 B2 | 11/2008 | Heuer et al. |
| 7,476,405 B2 | 1/2009 | Gardiner et al. |
| 7,906,154 B2 | 3/2011 | Heuer et al. |
| 8,293,269 B2 | 10/2012 | Ozeki et al. |
| 8,852,656 B2 | 10/2014 | Ozeki |
| 9,375,463 B2 | 6/2016 | Patel et al. |
| 9,445,624 B2 | 9/2016 | Xie et al. |
| 10,369,182 B2 | 8/2019 | Cohen |
| 10,857,195 B2 | 12/2020 | Ceddia et al. |
| 2004/0228934 A1 | 11/2004 | Stogniew et al. |
| 2006/0264497 A1 | 11/2006 | Zeligs |
| 2007/0264337 A1 | 11/2007 | Gardiner et al. |
| 2008/0131532 A1 | 6/2008 | Leitman et al. |
| 2008/0248141 A1 | 10/2008 | Heuer et al. |
| 2008/0248145 A1 | 10/2008 | Heuer et al. |
| 2013/0064803 A1* | 3/2013 | Naidu ............... A61P 25/00 424/94.6 |
| 2021/0038664 A1 | 2/2021 | Legge |
| 2021/0308081 A1 | 10/2021 | Nelson et al. |

FOREIGN PATENT DOCUMENTS

| | | |
|---|---|---|
| BE | 1020005 | 3/2013 |
| DE | 10255481 | 6/2005 |
| DE | 102009023549 | 12/2010 |
| EP | 0518468 | 12/1992 |
| EP | 1277468 | 1/2003 |

(Continued)

OTHER PUBLICATIONS

John Hopkins Medicine, https://www.hopkinsmedicine.org/health/wellness-and-prevention/sleepless-nights-try-stress-relief-techniques, Available Online Dec. 20, 2019, Wayback Machine (Year: 2019).*

(Continued)

*Primary Examiner* — Yih-Horng Shiao
*Assistant Examiner* — Jaret J Crews
(74) *Attorney, Agent, or Firm* — Scherrer Patent & Trademark Law, P.C.; Stephen T. Scherrer; Monique A. Morneault

(57) ABSTRACT

Compositions promote restful sleep and/or to a feeling of restful sleep. Specifically, the compositions of the present invention comprise a combination of hops extract, magnolia bark extract, melatonin, magnesium, rhodiola extract, L-theanine, vitamin B6, and spearmint extract and/or green tea extract to promote restful sleep and/or a feeling of restful sleep in an individual or animal. Methods of making and using the same are further provided.

18 Claims, 2 Drawing Sheets

(56) References Cited

FOREIGN PATENT DOCUMENTS

| | | |
|---|---|---|
| EP | 1743633 | 1/2007 |
| EP | 2060192 | 5/2009 |
| KR | 101720681 | 4/2017 |
| WO | 1997020485 | 6/1997 |
| WO | 2003024464 | 3/2003 |
| WO | 2008122099 | 10/2008 |
| WO | 2008122101 | 10/2008 |
| WO | 2010/002406 | 1/2010 |
| WO | 2017035631 | 3/2017 |
| WO | 2017109300 | 6/2017 |
| WO | WO-2019185439 A1 * | 10/2019 |

OTHER PUBLICATIONS

International Search Report and Written Opinion, PCT/US22/35825.

De Franciscis P, Grauso F, Luisi A, Schettino MT, Torella M, Colacurci N. Adding Agnus Castus and Magnolia to Soy Isoflavones Relieves Sleep Disturbances Besides Postmenopausal Vasomotor Symptoms-Long Term Safety and Effectiveness. Nutrients. 2017;9(2):129.

Talbott SM, Talbott JA, Pugh M. Effect of Magnolia officinalis and Phellodendron amurense (Relora®) on cortisol and psychological mood state in moderately stressed subjects. J Int Soc Sports Nutr. Aug. 7, 2013;10(1):37.

Kalman, D. S., Feldman, S., Feldman, R., Schwartz, H. I., Krieger, D. R., and Garrison, R. Effect of a proprietary Magnolia and Phellodendron extract on stress levels in healthy women: a pilot, double-blind, placebo-controlled clinical trial. Nutr J 2008;7:11.

Qu WM, Yue XF, Sun Y, Fan K, Chen CR, Hou YP, Urade Y, Huang ZL Honokiol promotes non-rapid eye movement sleep via the benzodiazepine site of the GABA(A) receptor in mice. Br J Pharmacol. Oct. 2012;167(3):587-98.

Nakazawa T, Yasuda T, Ohsawa K. Metabolites of orally administered Magnolia officinalis extract in rats and man and its antidepressant-like effects in mice. J Pharm Pharmacol 2003;55:1583-91.

Maruyama Y, Kuribara H, Kishi E, et al. Confirmation of the anxiolytic-like effect of dihydrohonokiol following behavioural and biochemical assessments. J Pharm Pharmacol 2001;53:721-5.

Kuribara H, Kishi E, Hattori N, et al. The anxiolytic effect of two oriental herbal drugs in Japan attributed to honokiol from magnolia bark. J Pharm Pharmacol 2000;52:1425-9.

Kuribara H, Kishi E, Maruyama Y. Does dihydrohonokiol, a potent anxiolytic compound, result in the development of benzodiazepine-like side effects? J Pharm Pharmacol 2000;52:1017-22.

Poivre M, Duez P. Biological activity and toxicity of the Chinese herb Magnolia officinalis Rehder & E. Wilson (Houpo) and its constituents J Zhejiang Univ Sci B. Mar. 2017.;18(3):194-214.

Woodbury A, Yu SP, Wei L, García P. Neuro-modulating effects of honokiol: a review. Front Neurol. Sep. 11, 2013;4:130.

Rhodiola/Cordyceps-Based Herbal Supplement Promotes Endurance Training-Improved Body Composition But Not Oxidative Stress and Metabolic Biomarkers: A Preliminary Randomized Controlled Study. Liao YH, Chao YC, Sim BY, Lin HM, Chen MT, Chen CY. Nutrients. Oct. 3, 2019;11(10):2357.

Effects of Rhodiola rosea supplementation on mental performance, physical capacity, and oxidative stress biomarkers in healthy men. Jówko E, Sadowski J, Długołęcka B, Gierczuk D, Opaszowski B, Cieśliński I. J Sport Health Sci. Oct. 2018;7(4):473-480.

Multicenter, open-label, exploratory clinical trial with Rhodiola rosea extract in patients suffering from burnout symptoms. Kasper S, Dienel A. Neuropsychiatr Dis Treat. Mar. 22, 2017;13:889-898.

Rhodiola rosea in Subjects with Prolonged or Chronic Fatigue Symptoms: Results of an Open-Label Clinical Trial. Lekomtseva Y, Zhukova I, Wacker A. Complement Med Res. 2017;24(1):46-52.

Rhodiola rosea Exerts Antiviral Activity in Athletes Following a Competitive Marathon Race. Ahmed M, Henson DA, Sanderson MC, Nieman DC, Zubeldia JM, Shanely RA. Front Nutr. Jul. 31, 2015;2:24.

Rhodiola rosea versus sertraline for major depressive disorder: A randomized placebo-controlled trial. Mao JJ, Xie SX, Zee J, Soeller I, Li QS, Rockwell K, Amsterdam JD. Phytomedicine. Mar. 15, 2015;22(3):394-9.

Rhodiola rosea for physical and mental fatigue: a systematic review. Ishaque S, Shamseer L, Bukutu C, et al. BMC Complementary and Alternative Medicine. 2012;12:70.

Reduction of acute mild stress corticosterone response and changes in stress-responsive gene expression in male Balb/c mice after repeated administration of a Rhodiola rosea L. root extract. Dinel AL, Guinobert I, Lucas C, Blondeau C, Bardot V, Ripoche I, Berthomier L, Pallet V, Layé S, Joffre C. Food Sci Nutr. 2019—22;7(11):3827-3841.

Assessing the Quality and Potential Efficacy of Commercial Extracts of Rhodiola rosea L. by Analyzing the Salidroside and Rosavin Content and the Electrophysiological Activity in Hippocampal Long-Term Potentiation, a Synaptic Model of Memory. Dimpfel W, Schombert L, Panossian AG. Front Pharmacol. 2018—24;9:425.

Anti-inflammatory effects of Rhodiola rosea L.: A review. Pu WL, Zhang MY, Bai RY, Sun LK, Li WH, Yu YL, Zhang Y, Song L, Wang ZX, Peng YF, Shi H, Zhou K, Li TX. Biomed Pharmacother. Jan. 2020;121:109552.

Rhodiola Rosea from the Selection of Traditional Applications to the Novel Phytotherapy for the Prevention and Treatment of Serious Disease Hamidpour R, Hamidpour S, Hamidpour M, Shahlari M, Sohraby M, Shahlari N, Hamidpour R. Global Journal of Medical Research: B Pharma, Drug Discovery, Toxicology and Medicine 15 (3) 1-10 (2015).

European Medicines Agency—Assessment report on Rhodiola rosea L., rhizoma et radix—Committee on Herbal Medicinal Products (HMPC)—Mar. 27, 2012 EMA/HMPC/232100/2011.

Rhodiola National Center for Complementary and Integrative Health https://www.nccih.nih.gov/health/rhodiola.

Benkherouf, A.; Logrén, N; Somborac, T; Kortesniemi, M; Soini, S.; Yang, B; Salo-Ahen, O.; Laaksonen, O; Uusi-Oukari, M. "Hops compounds modulatory effects and 6-prenylnaringenin dual mode of action on GABAA receptors". European Journal of Pharmacology. 873: 172962 (2020).

Fukudaa T, Ohnumab T, Obaraa K, Kondoc S, Araib H, Anoa Y. Supplementation with Matured Hop Bitter Acids Improves Cognitive Performance and Mood State in Healthy Older Adults with Subjective Cognitive Decline. J. Alzheimer's Disease 76 (2020) 387-398 387.

Ohara, K.; Misaizu, A.; Kaneko, Y.; Fukuda, T.; Miyake, M.; Miura, Y.; Okamura, H.; Yajima, J.; Tsuda, A. β-Eudesmol, an Oxygenized Sesquiterpene, Reduces the Increase in Saliva 3-Methoxy-4-Hydroxyphenylglycol After the "Trier Social Stress Test" in Healthy Humans: A Randomized, Double-Blind, Placebo-Controlled Cross-Over Study. Nutrients 2019, 11, 9.

Kyrou I, Christou A, Panagiotakos D, Stefanaki C, Skenderi K, Katsana K, Tsigos C. "Effects of a Hops (Humulus lupulus L.) Dry Extract Supplement on Self-Reported Depression, Anxiety and Stress Levels in Apparently Healthy Young Adults: A Randomized, Placebo-Controlled, Double-Blind, Crossover Pilot Study," Hormones 16, No. 2 (2017): 171-80.

Franco L, Sanchez C, Rodrguez AB, Baariga C, Romero RE. The sedative effect of non-alcoholic beer in healthy female nurses, PLOS one 2012a, 7(7): 1-6.

Cornu C, Remontet L, Noel-Baron F, Nicolas A, Feugier-Favier N, Roy P, Claustrat B, Saadatian-Elahi M, Kassaï B. A dietary supplement to improve the quality of sleep: a randomized placebo controlled trial. BMC Complement Altern Med. Jun. 22, 2010;10:29.

Scholey, S. Benson, A. Gibbs, N. Perry, J. Sarris, Murray G., Exploring the effect of LactiumTM and zizyphus complex on sleep quality: a double-blind, randomized placebo-controlled trial, Nutrients, vol. 9, No. 2, p. 154, 2017.

Maroo, N., Hazra, A. & Das, T. Efficacy and safety of a polyherbal sedative-hypnotic formulation NSF-3 in primary insomnia in comparison to zolpidem: a randomized controlled trial. Indian J Pharmacol 45, 34-39, (2013).

GRAS Notice No. GRN 000063.

Stein RM, Kang HJ, McCorvy JD, Glatfelter GC, Jones AJ, Che T, Slocum S, Huang XP, Savych O, Moroz YS, Stauch B, Johansson

(56) References Cited

OTHER PUBLICATIONS

LC, Cherezov V, Kenakin T, Irwin JJ, Shoichet BK, Roth BL, Dubocovich ML. Virtual discovery of melatonin receptor ligands to modulate circadian rhythms. Nature. Mar. 2020;579(7800):609-614.
Gobbi G, Comai S. Differential Function of Melatonin MT(1) and MT(2) Receptors in REM and NREM Sleep. Front Endocrinol (Lausanne). Mar. 1, 2019;10:87.
Ochoa-Sanchez R, Comai S, Lacoste B, Bambico FR, Dominguez-Lopez S, Spadoni G, Rivara S, Bedini A, Angeloni D, Fraschini F, Mor M, Tarzia G, Descarries L, Gobbi G. Promotion of non-rapid eye movement sleep and activation of reticular thalamic neurons by a novel MT2 melatonin receptor ligand. J Neurosci. Dec. 14, 2011;31(50):18439-52.
Sengupta A, Baba K, Mazzoni F, Pozdeyev NV, Strettoi E, Iuvone PM, Tosini G. Localization of melatonin receptor 1 in mouse retina and its role in the circadian regulation of the electroretinogram and dopamine levels. PLoS One. 2011;6(9):e24483.
Wang F, Li JC, Wu CF, Yang JY, Xu F, Peng F. Hypnotic activity of melatonin: involvement of semicarbazide hydrochloride, blocker of synthetic enzyme for GABA. Acta Pharmacol Sin. Sep. 2002;23(9):860-4.
Sletten, T. L., Magee, M., Murray, J. M., Gordon, C. J., Lovato, N., Kennaway, D. J., Gwini, S. M., Bartlett, D. J., Lockley, S. W., Lack, L. C., Grunstein, R. R., Rajaratnam, S., & Delayed Sleep on Melatonin (DelSoM) Study Group (2018). Efficacy of melatonin with behavioural sleep-wake scheduling for delayed sleep-wake phase disorder: A double-blind, randomised clinical trial. PLoS medicine, 15(6), e1002587.
Van Maanen A, Meijer AM, Smits MG, et al. Effects of melatonin and bright light treatment in childhood chronic sleep onset insomnia with late melatonin onset: a randomized controlled study. Sleep 2017;40(2).
Jain, S. V., Horn, P. S., Simakajornboon, N., Beebe, D. W., Holland, K., Byars, A. W., & Glauser, T. A. (2015). Melatonin improves sleep in children with epilepsy: a randomized, double-blind, crossover study. Sleep medicine, 16(5), 637-644.
Van Geijlswijk IM, van der Heijden KB, Egberts AC, Korzilius HP, Smits MG (2010) Dose finding of melatonin for chronic idiopathic childhood sleep onset insomnia: an RCT. Psychopharmacology (Berl) 212: 379-391.
Mundey K, Benloucif S, Harsanyi K, Dubocovich ML, Zee PC (2005) Phase-dependent treatment of delayed sleep phase syndrome with melatonin. Sleep 28: 1271-1278.
Rajaratnam, S. M., Middleton, B., Stone, B. M., Arendt, J., & Dijk, D. J. (2004). Melatonin advances the circadian timing of EEG sleep and directly facilitates sleep without altering its duration in extended sleep opportunities in humans. The Journal of physiology, 561(Pt 1), 339-351.
Almeida Montes LG, Ontiveros Uribe MP, Cortes Sotres J, Heinze Martin G (2003) Treatment of primary insomnia with melatonin: a double-blind, placebo-controlled, crossover study. J Psychiatry Neurosci 28: 191-196.
Zhdanova IV, Wurtman RJ, Regan MM, Taylor JA, Shi JP, et al. (2001) Melatonin treatment for age-related insomnia. J Clin Endocrinol Metab 86: 4727-4730.
Haimov I, Lavie P, Laudon M, Herer P, Vigder C, et al. (1995) Melatonin replacement therapy of elderly insomniacs. Sleep 18: 598-603.
Costello, R. B., Lentino, C. V., Boyd, C. C., O'Connell, M. L., Crawford, C. C., Sprengel, M. L., & Deuster, P. A. (2014). The effectiveness of melatonin for promoting healthy sleep: a rapid evidence assessment of the literature. Nutrition journal, 13, 106.
Masters, A., Pandi-Perumal, S. R., Seixas, A., Girardin, J. L., & McFarlane, S. I. (2014). Melatonin, the Hormone of Darkness: From Sleep Promotion to Ebola Treatment. Brain disorders & therapy, 4(1), 1000151.
Ferracioli-Oda E, Qawasmi A, Bloch MH. Meta-analysis: melatonin for the treatment of primary sleep disorders. PLoS One. May 17, 2013;8(5):e63773.

Buscemi N, Vandermeer B, Hooton N, Pandya R, Tjosvold L, Hartling L, Baker G, Klassen TP, Vohra S. The efficacy and safety of exogenous melatonin for primary sleep disorders. A meta-analysis. J Gen Intern Med. Dec. 2005;20(12):1151-8.
Sanchez REA, Kalume F, de la Iglesia HO. Sleep timing and the circadian clock in mammals: Past, present and the road ahead. Semin Cell Dev Biol. Jun. 3, 2021:S1084-9521(21)00149-X.
Che T, Yan C, Tian D, Zhang X, Liu X, Wu Z The Association Between Sleep and Metabolic Syndrome: A Systematic Review and Meta-Analysis. Front Endocrinol (Lausanne). Nov. 19, 2021;12:773646.
Moody OA, Zhang ER, Vincent KF, Kato R, Melonakos ED, Nehs CJ, Solt K. The Neural Circuits Underlying General Anesthesia and Sleep. Anesth Analg. May 1, 2021;132(5):1254-1264.
Falup-Pecurariu C, Diaconu Ş, Ţînţ D, Falup-Pecurariu O. Neurobiology of sleep (Review). Exp Ther Med. Mar. 2021;21(3):272.
Dorsey A, de Lecea L, Jennings KJ. Neurobiological and Hormonal Mechanisms Regulating Women's Sleep. Front Neurosci. Jan. 14, 2021;14:625397.
Madari S, Golebiowski R, Mansukhani MP, Kolla BP. Pharmacological Management of Insomnia. Neurotherapeutics. Jan. 2021;18(1):44-52.
Patty Taddei-Allen. Economic Burden and Managed Care Considerations for the Treatment of Insomnia. Am J Manag Care. 2020;26:S91-S96.
Gotter AL, Garson SL, Stevens J, Munden RL, Fox SV, Tannenbaum PL, Yao L, Kuduk SD, McDonald T, Uslaner JM, Tye SJ, Coleman PJ, Winrow CJ, Renger JJ. Differential sleep-promoting effects of dual orexin receptor antagonists and GABAA receptor modulators. BMC Neurosci. Sep. 22, 2014;15:109.
Hu Z, Lee CI, Shah VK, Oh EH, Han JY, Bae JR, Lee K, Chong MS, Hong JT, Oh KW. Cordycepin Increases Nonrapid Eye Movement Sleep via Adenosine Receptors in Rats. Evid Based Complement Alternat Med. 2013;2013:840134.
Lancel M. Role of GABAA receptors in the regulation of sleep: initial sleep responses to peripherally administered modulators and agonists. Sleep. Feb. 1, 1999;22(1):33-42.
Cao Y, Zhen S, Taylor AW, Appleton S, Atlantis E, Shi Z. Magnesium Intake and Sleep Disorder Symptoms: Findings from the Jiangsu Nutrition Study of Chinese Adults at Five-Year Follow-Up. Nutrients. Sep. 21, 2018;10(10).
Scholey A, Benson S, Gibbs A, Perry N, Sarris J, Murray G. Exploring the Effect of Lactium™ and Zizyphus Complex on Sleep Quality: A Double-Blind, Randomized Placebo-Controlled Trial. Nutrients. Feb. 17, 2017;9(2). pii: E154.
Murck H, Steiger A. Mg2+ reduces ACTH secretion and enhances spindle power without changing delta power during sleep in men—possible therapeutic implications. Psychopharmacology (Berl). Jun. 1998;137(3):247-52.
Tanabe, K., Yamamoto, A., Suzuki, N., Osada, N., Yokoyama, Y., Samejima, H., Seki, A., Oya, M., Murabayashi, T., Nakayama, M., Yamamoto, M., Omiya, K., Itoh, H., and Murayama, M. Efficacy of oral magnesium administration on decreased exercise tolerance in a state of chronic sleep deprivation. Jpn.Circ.J 1998;62(5):341-346.
Roguin Maor N, Alperin M, Shturman E, Khairaldeen H, Friedman M, Karkabi K, Milman U. Effect of Magnesium Oxide Supplementation on Nocturnal Leg Cramps: A Randomized ClinicalTrial. JAMA Intern Med. May 1, 2017;177(5):617-623.
Sebo P, Cerutti B, Haller DM. Effect of magnesium therapy on nocturnal leg cramps: a systematic review of randomized controlled trials with meta-analysis using simulations. Fam Pract. Feb. 2014;31(1):7-19.
Hornyak M, Voderholzer U, Hohagen F, et al. Magnesium therapy for periodic leg movements-related insomnia and restless legs syndrome: an open pilot study. Sleep 1998;21:501-5.
Phelan D, Molero P, Martínez-González M, Molendijk M. Magnesium and mood disorders: systematic review and meta-analysis BJPsych Open. Jul. 2018; 4(4): 167-179.
Pouteau E, Kabir-Ahmadi M, Noah L, Mazur A, Dye L, Hellhammer J, Pickering G, Dubray C. Superiority of magnesium and vitamin B6 over magnesium alone on severe stress in healthy adults with low magnesemia: A randomized, single-blind clinical trial. PLoS One. 2018; 13(12): e0208454.

(56) References Cited

OTHER PUBLICATIONS

Boyle N.B., C. Lawton, L. Dye. The Effects of Magnesium Supplementation on Subjective Anxiety and Stress—A Systematic Review. Nutrients. May 2017; 9(5): 429.
Nielsen FH, Johnson LK, Zeng H. Magnesium supplementation improves indicators of low magnesium status and inflammatory stress in adults older than 51 years with poor quality sleep. Magnes Res. Dec. 2010;23(4):158-68.
Takase B, Akima T, Uehata A, Ohsuzu F, Kurita A. Effect of chronic stress and sleep deprivation on both flow-mediated dilation in the brachial artery and the intracellular magnesium level in humans. Clin Cardiol. Apr. 2004,27(4):223-7.
Durlach J, Pagès N, Bac P, Bara M, Guiet-Bara A. Magnesium depletion with hypo- or hyper-function of the biological clock may be involved in chronopathological forms of asthma. Magnes Res. Mar. 2005;18(1):19-34.
Jacobsen RB, Ulrich D, Huguenard JR. GABA(B) and NMDA receptors contribute to spindle-like oscillations in rat thalamus in vitro. J Neurophysiol. Sep. 2001;86(3):1365-75.
Depoortere, H.; Francon, D.; Llopis, J. Effects of a Magnesium-Deficient Diet on Sleep Organization in Rats. Neuropsychobiology 1993, 27, 237-245.
Poenaru, S.; Rouhani, S.; Durlach, J.; Aymard, N.; Belkahla, F.; Rayssiguier, Y.; Iovino, M. Vigilance States and Cerebral Monoamine Metabolism in Experimental Magnesium Deficiency. Magnesium 1984, 3, 145-151.
Holst, S.C.; Valomon, A.; Landolt, H.P. Sleep Pharmacogenetics: Personalized Sleep-Wake Therapy. Annu. Rev. Pharmacol. Toxicol. 2016, 56, 577-603.
Sharma P, Chung C, Vizcaychipi M. Magnesium: The Neglected Electrolyte? A Clinical Review. Pharmacology & Pharmacy, 2014, 5, 762-772.
Kolla, B. P., Mansukhani, M. P., and Schneekloth, T. Pharmacological treatment of insomnia in alcohol recovery: a systematic review. Alcohol Alcohol 2011;46(5):578-585.
Magnesium. WebMD 2017.
NCT00833092—Magnesium Nutrition and Sleep Behavior in Older Adults—ClinicalTrials.gov Jul. 27, 2011.
NCT02363634—Clinical Trial to Evaluate Magtein in Older Adults—ClinicalTrials.gov. Feb. 16, 2015.
Unno K, Noda S, Kawasaki Y, Yamada H, Morita A, Iguchi K, Nakamura Y. Ingestion of green tea with lowered caffeine improves sleep quality of the elderly via suppression of stress. J Clin Biochem Nutr. Nov. 2017;61(3):210-216.
Unno K, Noda S, Kawasaki Y, Yamada H, Morita A, Iguchi K, Nakamura Y. Reduced Stress and Improved Sleep Quality Caused by Green Tea Are Associated with a Reduced Caffeine Content. Nutrients. Jul. 19, 2017;9(7). pii: E777.
Unno K, Furushima D, Hamamoto S, Iguchi K, Yamada H, Morita A, Horie H, Nakamura Y. Stress-Reducing Function of Matcha Green Tea in Animal Experiments and Clinical Trials. Nutrients. Oct. 10, 2018;10(10). pii: E1468.
Unno K, Yamada H, Iguchi K, Ishida H, Iwao Y, Morita A, Nakamura Y. Anti-stress Effect of Green Tea with Lowered Caffeine on Humans: A Pilot Study. Biol Pharm Bull. 2017;40(6):902-909.
White DJ, de Klerk S, Woods W, Gondalia S, Noonan C, Scholey AB. Anti-Stress, Behavioural and Magnetoencephalography Effects of an L-Theanine-Based NutrientDrink: A Randomised, Double-Blind, Placebo-Controlled, Crossover Trial. Nutrients. Jan. 19, 2016;8(1). pii.
Hidese S, Ota M, Wakabayashi C, Noda T, Ozawa H, Okubo T, Kunugi H. Effects of chronic l-theanine administration in patients with major depressive disorder: an open-label study. Acta Neuropsychiatr. Apr. 2017;29(2):72-79.
Dodd FL, Kennedy DO, Riby LM, Haskell-Ramsay CF. A double-blind, placebo-controlled study evaluating the effects of caffeine and L-theanine both alone and in combination on cerebral blood flow, cognition and mood. Psychopharmacology (Berl). Jul. 2015;232(14):2563-76.
Nobre AC, Rao A, Owen GN. L-theanine, a natural constituent in tea, and its effect on mental state. Asia Pac J Clin Nutr. 2008;17 Suppl 1:167-8.
Kelly SP, Gomez-Ramirez M, Montesi JL, Foxe JJ. L-theanine and caffeine in combination affect human cognition as evidenced by oscillatory alpha-band activity and attention task performance. J Nutr. Aug. 2008;138(8):1572S-1577S.
Murakami S, Kurihara S, Koikawa N, Nakamura A, Aoki K, Yosigi H, Sawaki K, Ohtani M. Effects of oral supplementation with cystine and theanine on the immune function of athletes in endurance exercise: randomized, double-blind, placebo-controlled trial. Biosci Biotechnol Biochem. Apr. 23, 2009;73(4):817-21.
Wang D, Gao Q, Wang T, Qian F, Wang Y. Theanine: the unique amino acid in the tea plant as an oral hepatoprotective agent. Asia Pac J Clin Nutr. May 2017;26(3):384-391. Review.
Camfield DA, Stough C, Farrimond J, Scholey AB. Acute effects of tea constituents L-theanine, caffeine, and epigallocatechin gallate on cognitive function and mood: a systematic review and meta-analysis. Nutr Rev. Aug. 2014;72(8):507-22. Review.
Einöther SJ, Martens VE. Acute effects of tea consumption on attention and mood. Am J Clin Nutr. Dec. 2013;98(6 Suppl):1700S-1708S. Review.
Barrett JR, Tracy DK, Giaroli G. To sleep or not to sleep: a systematic review of the literature of pharmacological treatments of insomnia in children and adolescents with attention deficit/hyperactivity disorder. J Child Adolesc Psychopharmacol. Dec. 2013;23(10):640-7. Review.
L-Theanine. Alternative Medicine Review. 2005; 10 (2):136-138.
Theanine. WebMD 2016.
Scientific Opinion on the substantiation of health claims related to L-theanine . . . EFSA Panel on Dietetic Products, Nutrition and Allergies (NDA) European Food Safety Authority (EFSA), Parma, Italy. EFSA Journal 2011;9(6):2238.
Taiyo L-Theanine Suntheanine Research (Apr. 2008).
Sateia, M. J., Buysse, D. J., Krystal, A. D., Neubauer, D. N., & Heald, J. L. (2017). Clinical Practice Guideline for the Pharmacologic Treatment of Chronic Insomnia in Adults: An American Academy of Sleep Medicine Clinical Practice Guideline. Journal of clinical sleep medicin 13(2), 307-349.
Kwon YO, Hong JT, Oh KW. Rosmarinic Acid Potentiates Pentobarbital-Induced Sleep Behaviors and Non-Rapid Eye Movement (NREM) Sleep through the Activation of GABA(A)-ergic Systems. Biomol Ther (Seoul). Mar. 1, 2017;25(2):105-111.
Ito N, Yabe T, Gamo Y, Nagai T, Oikawa T, Yamada H, Hanawa T. Rosmarinic acid from Perillae Herba produces an antidepressant-like effect in mice through cell proliferation in the hippocampus. Biol Pharm Bull. Jul. 2008;31(7):1376-80.
Tubbs AS, Kennedy KER, Alfonso-Miller P, Wills CCA, Grandner MA. A Randomized, Double-Blind, Placebo-Controlled Trial of a Polyphenol Botanical Blend on Sleep and Daytime Functioning. Int J Environ Res Public Health. Mar. 16, 2021;18(6):3044.
Caro DC, Rivera DE, Ocampo Y, Franco LA, Salas RD. Pharmacological Evaluation of *Mentha spicata* L. and *Plantago major* L., Medicinal Plants Used to Treat Anxiety and Insomnia in Colombian Caribbean Coast. Evid Based Complement Alternat Med. Aug. 7, 2018;2018:5921514.
FDA2012b. Substances generally recognized as safe: Spices and other natural seasonings and flavorings.12CRF182.10.

\* cited by examiner

COMPOSITION FOR PROMOTING RESTFUL SLEEP AND METHODS OF MAKING AND USING THE SAME

CROSS-REFERENCE TO RELATED APPLICATIONS

The present invention claims priority to U.S. Prov. Pat. App. No. 63/218,457 titled "Composition and Method for Promoting a Feeling of Restful Sleep," filed Jul. 5, 2021, which is incorporated herein by reference in its entirety.

TECHNICAL FIELD

The present invention relates to compositions conducive to the promotion of restful sleep and/or to a feeling of restful sleep. Specifically, the compositions of the present invention comprise a combination of hops extract, magnolia bark extract, melatonin, magnesium, rhodiola extract, L-theanine, vitamin B6, and spearmint extract and/or green tea extract to promote restful sleep and/or a feeling of restful sleep in an individual or animal. Methods of making and using the same are further provided.

BACKGROUND

Sleep is a recurrent and transient state of reduced physical and sensory activity covering a significant portion of people's and animal's lives. This natural biological process plays a critical role in health and is essential to mental and physical well-being. Insomnia, on the other hand, is defined as difficulty in falling or staying asleep and effects about one-third of the adult population in North America. Chronic insomnia is associated with decreased quality of life and increased disease risk. Problems with insomnia are so vast that these issues can impact the economy.

Sleep is the fruit of a complex dynamic process, driven by a physiological need, under the control of endogenous chemicals and select brain neural structures that are influenced by environmental factors.

In mammals, sleep is typically induced by internal homeostatic and circadian mechanisms working in harmony to regulate the daily sleep/wake cycle. The homeostatic drive tracks our need for sleep in relation to wakefulness duration, while the circadian system tracks the light/dark rhythm to align activity with the photoperiod.

In humans, the transition from wakefulness to sleep typically occurs at night when the need for sleep is high and circadian signals maintaining wakefulness drop. This phenomenon is generally accompanied by an increase in melatonin, decrease in cortisol, and a drop in core temperature. Over the years, the nature of the neuronal and hormonal components impacting this "flip/flop" mechanism driving the sleep/wake transition, itself governed by homeostatic factors, has been unveiled and understood.

These findings highlight major roles for gamma-aminobutyric acid (GABA), the main inhibitory neurotransmitter of the central nervous system, in the promotion of sleep and of the neuropeptide, orexin, in the regulation of arousal. In addition, accumulation of adenosine in the basal forebrain throughout wakeful time is also sleep inducing.

Both sleep inducing neurotransmitters (GABA and adenosine) act as agonist on membrane receptors which can be ion channels for GABA or G protein coupled receptors (GPCRs) for adenosine. Drugs, such as benzodiazepines that are widely used as hypnotics, sedatives or tranquilizers promote the action of GABA and GABA-AA receptors while the widely consumed stimulant, caffeine, act as antagonists at adenosine Al receptors, thus preventing sleep induction.

The pineal gland produced hormone melatonin is capable of inducing sleepiness and improving night sleep. Melatonin acts through GPCRs inhibiting neuronal populations and acting as a mediator between environmental cues (i.e., light) and the sleep cycle.

While much understanding of the sleep cycle and various neurotransmitters has increased over the past several years, current sleep treatments are either ineffective or not effective enough to solve issues with insomnia. A need, therefore, exists for improved compositions and methods of making and using the same for promoting restful sleep. Specifically, improved compositions and methods of making and using the same are needed to promote restful sleep and feelings of restful sleep in a user. More specifically, improved compositions and methods of making and using the same are needed to allow a user to easily and effectively achieve a state of restful sleep.

Moreover, a need exists for improved compositions and methods of making and using the same that is accomplished using various common ingredients. Specifically, a need exists for compositions and methods of making and using the same that utilizes a plurality of plant extracts or otherwise purified compounds extracted from plants. More specifically, a need exists for compositions and methods of using the same that utilizes a blend of at least eight extracts or purified compounds combined together into a blend that may be easily administered or ingested by a user thereof.

In addition, a need exists for improved compositions and methods of making and using the same that is effective without harmful side effects. Specifically, a need exists for improved compositions and methods of making and using the same that will not lead to intolerance, dependency, or addiction issues, and/or withdrawal problems.

Further, a need exists for improved compositions and methods of making and using the same that may be utilized by humans as well as other creatures, such as pets. Specifically, a need exists for improved compositions and methods of making and using the same that may be in the form of beverages, foods, supplements, snacks, pet treats and pet food, tinctures, or in other like forms that may be easily administered to a user thereof.

SUMMARY OF THE INVENTION

The present invention relates to compositions conducive to the promotion of restful sleep and/or to a feeling of restful sleep. Specifically, the compositions of the present invention comprise a combination of hops extract, magnolia bark extract, melatonin, magnesium, rhodiola extract, L-theanine, vitamin B6, and spearmint extract and/or green tea extract to promote restful sleep and/or a feeling of restful sleep in an individual or animal. Methods of making and using the same are further provided.

To this end, in an embodiment of the present invention, a dietary composition formulated in a therapeutic effective amount to promote restful sleep in humans or animals is provided. The dietary composition comprises a blend of: a first substance selected from the group of humulone, xanthohumol, myrcenol, and combinations thereof; a second substance selected from the group of honokiol, magnolol, and combinations thereof; melatonin; L-theanine; magnesium; a third substance selected from the group of rosavine, tyrosol, salidroside, and combinations thereof; a fourth substance selected from the group of rosmarinic acid, epigallocatechin gallate, and combinations thereof; and vitamin B6.

In an embodiment, the first substance is derived from hops.

In an embodiment, the first substance is in the form of hops extract.

In an embodiment, the third substance is derived from rhodiola.

In an embodiment, the third substance is in the form of rhodiola extract.

In an embodiment, the fourth substance is derived from an ingredient selected from the group of spearmint, green tea, and a blend thereof.

In an embodiment, the fourth substance is in the form of an ingredient selected from the group of spearmint extract, green tea extract, and a blend thereof.

In an embodiment, the second substance is derived from magnolia.

In an embodiment, the second substance is in the form of magnolia bark extract.

In an embodiment, the first substance is from hops extract and the hops extract is present in the blend in an amount between about 0.1% and about 70%, wherein the second substance is from magnolia bark extract and the magnolia bark extract is present in the blend in an amount between about 0.1% and about 65%, wherein the melatonin is present in the blend in an amount between about 0.1% and about 75%, wherein the magnesium is present in the blend in an amount between about 0.1% and about 75%, wherein the third substance is from rhodiola extract and the rhodiola extract is present in the blend in an amount between about 0.1% and about 80%, wherein L-theanine is present in the blend in an amount between about 0.1% and about 75%, wherein the fourth substance is from an ingredient selected from the group of spearmint extract, green tea extract, and a combination thereof and the ingredient is present in the blend in an amount between about 0.1% and about 95%, and the vitamin B6 is present in the blend in an amount between about 0.01% and about 30%.

In an embodiment, the first substance is from hops extract and the hops extract is present in the blend in an amount between about 1% and about 20%, wherein the second substance is from magnolia bark extract and the magnolia bark extract is present in the blend in an amount between about 1% and about 40%, wherein the melatonin is present in the blend in an amount between about 0.1% and about 10%, wherein the magnesium is present in the blend in an amount between about 1% and about 40%, wherein the third substance is from rhodiola extract and the rhodiola extract is present in the blend in an amount between about 1% and about 40%, wherein L-theanine is present in the blend in an amount between about 1% and about 50%, wherein the fourth substance is from an ingredient selected from the group of spearmint extract, green tea extract, and combinations thereof and the ingredient is present in the blend in an amount between about 1% and about 60%, and the vitamin B6 is present in the blend in an amount between about 0.1% and about 10%.

In an embodiment, the first substance is from hops extract and the hops extract is present in the dietary composition in an amount between about 10 mg and about 500 mg, wherein the second substance is from magnolia bark extract and the magnolia bark extract is present in the dietary composition in amount between about 5 mg and about 400 mg, wherein the melatonin is present in the dietary composition in an amount between about 0.5 mg and about 700 mg, wherein the magnesium is present in the dietary composition in an amount between about 10 mg and about 350 mg, wherein the third substance is from rhodiola extract and the rhodiola extract is present in the dietary composition in an amount between about 20 mg and about 1000 mg, wherein L-theanine is present in the dietary composition in an amount between about 20 mg and about 600 mg, wherein the fourth substance is from an ingredient selected from the group of spearmint extract, green tea extract, and combinations thereof and the ingredient is present in the dietary composition in an amount between about 200 mg and about 800 mg, and the vitamin B6 is present in the dietary composition in an amount between about 2 mg and about 100 mg.

In an embodiment, the first substance is from hops extract and the hops extract is present in the dietary composition in an amount between about 15 mg and about 35 mg, wherein the second substance is from magnolia bark extract and the magnolia bark extract is present in the dietary composition in amount between about 50 mg and about 150 mg, wherein the melatonin is present in the dietary composition in an amount between about 1 mg and about 3 mg, wherein the magnesium is present in the dietary composition in an amount between about 100 mg and about 300 mg, wherein the third substance is from rhodiola extract and the rhodiola extract is present in the dietary composition in an amount between about 100 mg and about 500 mg, wherein L-theanine is present in the dietary composition in an amount between about 100 mg and about 400 mg, wherein the fourth substance is from an ingredient selected from the group of spearmint extract, green tea extract, and combinations thereof and the ingredient is present in the dietary composition in an amount between about 300 mg and about 600 mg, and the vitamin B6 is present in the dietary composition in an amount between about 5 mg and about 50 mg.

In an embodiment, the first substance is from hops extract and the hops extract is present in the dietary composition in an amount of about 20 mg, wherein the second substance is from magnolia bark extract and the magnolia bark extract is present in the dietary composition in amount of about 100 mg, wherein the melatonin is present in the dietary composition in an amount of about 2 mg, wherein the magnesium is present in the dietary composition in an amount of about 200 mg, wherein the third substance is from rhodiola extract and the rhodiola extract is present in the dietary composition in an amount of about 200 mg, wherein L-theanine is present in the dietary composition in an amount of about 200 mg, wherein the fourth substance is from an ingredient selected from the group of spearmint extract, green tea extract, and combinations thereof and the ingredient is present in the dietary composition in an amount of about 485 mg, and the vitamin B6 is present in the dietary composition in an amount of about 10 mg.

In an embodiment, the dietary composition is in the form of a pill, a capsule, a tablet, a softgel, a lozenge, a powder, a liquid, a food, a beverage, a gummy, or an orally-dissolving film strip.

In an alternate embodiment of the present invention, a method of promoting restful sleep in humans or animals is provided. The method comprises the steps of: providing a dietary composition formulated in a therapeutic effective amount to promote restful sleep in humans or animals comprising a blend of a first substance selected from the group of humulone, xanthohumol, myrcenol, and combinations thereof; a second substance selected from the group of honokiol, magnolol, and combinations thereof; melatonin; L-theanine; magnesium; a third substance selected from the group of rosavine, tyrosol, salidroside, and combinations thereof; a fourth substance selected from the group of rosmarinic acid, epigallocatechin gallate, and combinations thereof; and vitamin B6; and forming the dietary composition into an ingestible form.

In an embodiment, the first substance is from hops extract, the second substance is from magnolia bark extract, the third substance is from rhodiola extract, and the fourth substance is from an ingredient selected from the group of spearmint extract, green tea extract, and a combination thereof.

In an embodiment, the hops extract is present in the blend in an amount between about 0.1% and about 70%, the magnolia bark extract is present in the blend in an amount between about 0.1% and about 65%, wherein the melatonin is present in the blend in an amount between about 0.1% and about 75%, wherein the magnesium is present in the blend in an amount between about 0.1% and about 75%, wherein the rhodiola extract is present in the blend in an amount between about 0.1% and about 80%, wherein L-theanine is present in the blend in an amount between about 0.1% and about 75%, wherein the ingredient selected from the group of spearmint extract, green tea extract, and a combination thereof is present in the blend in an amount between about 0.1% and about 95%, and the vitamin B6 is present in the blend in an amount between about 0.01% and about 30%.

In an embodiment, the hops extract is present in the dietary composition in an amount between about 10 mg and about 500 mg, wherein the magnolia extract is present in the dietary composition in an amount between about 5 mg and about 400 mg, wherein the melatonin is present in the dietary composition in an amount between about 0.5 mg and about 700 mg, wherein the magnesium is present in the dietary composition in an amount between about 10 mg and about 350 mg, wherein the second substance is from rhodiola extract and the rhodiola extract is present in the dietary composition in an amount between about 20 mg and about 1000 mg, wherein L-theanine is present in the dietary composition in an amount between about 20 mg and about 600 mg, wherein the ingredient selected from the group of spearmint extract, green tea extract, and a combination thereof is present in an amount between about 200 mg and about 800 mg, and the vitamin B6 is present in the dietary composition in an amount between about 2 mg and about 100 mg.

In an embodiment, the form is a pill, a capsule, a tablet, a softgel, a lozenge, a powder, a liquid, a gummy, a beverage, a food, or an orally-dissolving film strip.

It is, therefore, an advantage and objective of the present invention to provide improved compositions and methods of making and using the same for promoting restful sleep.

Specifically, it is an advantage and objective of the present invention to provide improved compositions and methods of making and using the same are needed to promote restful sleep and feelings of restful sleep in a user.

More specifically, it is an advantage and objective of the present invention to provide improved compositions and methods of making and using the same are needed to allow a user to easily and effectively achieve a state of restful sleep.

Moreover, it is an advantage and objective of the present invention to provide improved compositions and methods of making and using the same that is accomplished using various common ingredients.

Specifically, it is an advantage and objective of the present invention to provide compositions and methods of making and using the same that utilizes a plurality of plant extracts or otherwise purified compounds extracted from plants.

More specifically, it is an advantage and objective of the present invention to provide compositions and methods of using the same that utilizes a blend of at least eight extracts or purified compounds combined together into a blend that may be easily administered or ingested by a user thereof.

In addition, it is an advantage and objective of the present invention to provide improved compositions and methods of making and using the same that is effective without harmful side effects.

Specifically, it is an advantage and objective of the present invention to provide improved compositions and methods of making and using the same that will not lead to intolerance, dependency, or addiction issues, and/or withdrawal problems.

Further, it is an advantage and objective of the present invention to provide improved compositions and methods of making and using the same that may be utilized by humans as well as other creatures, such as pets.

Specifically, it is an advantage and objective of the present invention to provide improved compositions and methods of making and using the same that may be in the form of beverages, foods, supplements, snacks, pet treats and pet food, tinctures, orally-dissolving strips, or in other like forms that may be easily administered to a user thereof.

Additional features and advantages of the present invention are described in, and will be apparent from, the detailed description of the presently preferred embodiments and from the drawings.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE PRESENTLY PREFERRED EMBODIMENTS

Figure 1:
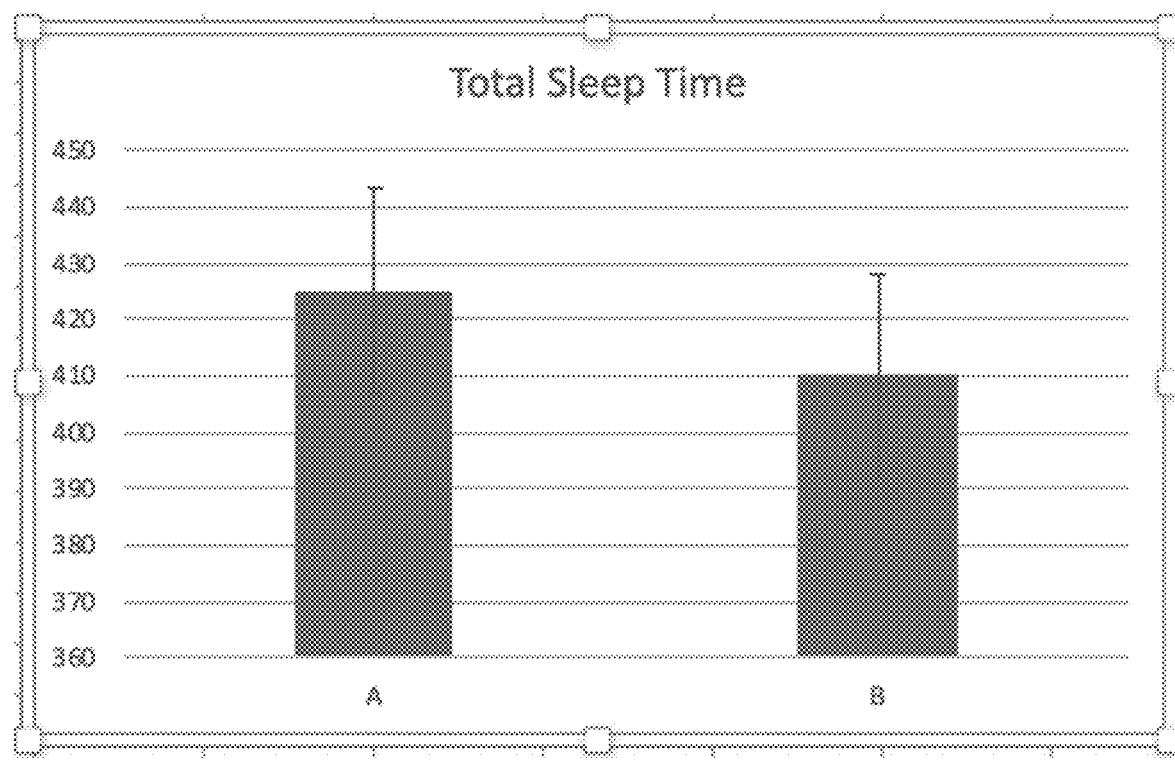
FIG. 1 illustrates a graph comparing observed total sleep time over two weeks in subjects taking the Beverage A (A) and subjects taking Beverage B (B) in an embodiment of the present invention.

The present invention relates to compositions conducive to the promotion of restful sleep and/or to a feeling of restful sleep. Specifically, the compositions of the present invention comprise a combination of hops extract, magnolia bark extract, melatonin, magnesium, rhodiola extract, L-theanine, vitamin B6, and spearmint extract and/or green tea extract to promote restful sleep and/or a feeling of restful sleep in an individual or animal. Methods of making and using the same are further provided.

For the purposes of the present invention, the term "restful sleep" is defined as falling asleep promptly and sleeping enough to feel refreshed. As such, "restful sleep" can be measured by objective and subjective means.

The composition of the present invention, described herein, is designed to target biological components promoting and supporting a feeling of restful sleep, including cortisol, GABA, and melatonin systems while supporting body recovery and mood stabilization.

The composition of the present invention comprises various amounts of extracts or ingredients (i.e., purified compounds derived from plants) that are combined together into a blend that is designed to promote a feeling of restful sleep.

Preferably, the present invention comprises a blend of ingredients that is soluble in aqueous media. Specifically, the composition of the present invention is preferably administered in the form of a beverage or a food that may be ingestible by a user thereof. Other forms of the composition of the present invention may include pills, capsules, tablets, softgels, lozenges, powders, liquids, and gummies. The present invention as described herein may be ingested by humans and/or animals, such as pets.

In an embodiment of the present invention, the composition may comprise a blend of a first substance selected from the group of humulone, xanthohumol, myrcenol, and combinations thereof, rosmarinic acid and/or epigallocatechin gallate (ECGC), honokiol and/or magnolol, L-theanine, melatonin, magnesium, vitamin B6, and a second substance selected from the group of rosavine, salidroside, and combinations thereof, in therapeutic effective amounts to promote restful sleep and/or a feeling of restful sleep in humans and/or animals after ingesting the same. Specifically, the first substance may be derived from hops, and preferably is present in hops extract that may be incorporated into the composition. In a preferred embodiment, the substance comprises a combination of humulone, xanthohumol, and myrcenol. Moreover, the rosmarinic acid may preferably be present in spearmint extract and the ECGC may be present in green tea extract that may be incorporated into the composition. In addition, the honokiol and/or magnolol may be derived from magnolia, and preferably is present in magnolia bark extract that may be incorporated into the composition.

In a preferred embodiment of the present invention, the composition may comprise a blend of hops extract, magnolia extract, rhodiola extract, spearmint extract and/or green tea extract, L-theanine, melatonin, magnesium, and vitamin B6 in therapeutically effective amounts to promote restful sleep and/or a feeling of restful sleep after ingesting the same. Specifically, the composition may comprise a blend thereof of the ingredients listed above in the following ranges: between about 0.1% and about 70% hops extract, between about 0.1% and about 65% magnolia extract, between about 0.01% and about 75% melatonin, between about 0.1% and about 75% L-theanine, between about 0.1% and about 75% magnesium, between about 0.1% and about 80% rhodiola extract, between about 0.1% and about 95% spearmint extract, green tea extract, or a blend of spearmint extract and green tea extract, and between about 0.01% and about 30% vitamin B6.

More preferably, the composition may comprise a blend thereof of ingredients listed above in the following ranges: between about 1% and about 20% hops extract, between about 1% and about 40% magnolia extract, between about 0.1 and about 10% melatonin, between about 1% and about 50% L-theanine, between about 1% and about 40% magnesium, between about 1% and about 40% rhodiola extract, between about 1% and about 60% spearmint extract, green tea extract, or a blend of spearmint extract and green tea extract, and between about 0.1% and about 10% vitamin B6.

Most preferably, the composition may comprise a blend thereof of the ingredients listed above in the following amounts: about 1.6% hops extract, about 8.2% magnolia extract, about 0.16% melatonin, about 16.4% L-theanine, about 16.4% magnesium, about 16.4% rhodiola extract, about 39.9% spearmint extract, green tea extract, or a blend of spearmint extract and green tea extract, and about 0.82% vitamin B6.

The compositions of the present invention may further comprise excipients and/or emulsifiers, sweeteners, bulking agents, mouthfeel and/or flavor agents, and other agents or ingredients suitable for food and/or beverage compositions. It should be noted that the amounts and percentages preferred in the present invention are measured against the total of the blend of the active ingredients listed above without regard to additional ingredients are provided in the compositions described herein.

Hops

Hops (Humulus lupulus) is an important agricultural perennial plant that has been traditionally used to flavor beer. Hops flavors for beer are typically produced from the cones and flowers of the plant, which are rich in flavonoids, phenolic acids, aromatic oils, tannins, and resins. Besides its use in the beer industry, hops extracts have been used as sedatives to reduce anxiety and help sleep. Pre-clinical trial studies both in animals and cellular models have demonstrated sleep enhancing and anxiolytic activity presumably by interacting with the GABA-A and serotonin systems, which are known to be involved in the sleep process. In humans, hops in polyherbal blends of plants known for their sedative properties has been shown to be effective to improve sleep quality. A combination of Valerian and hops has been shown to be particularly effective by acting concomitantly on the adenosine, melatonin, and GABA-A systems that regulate sleep.

In an embodiment of the present invention, the composition may include hops extract, specifically hops cone extract. A serving of the composition may include from about 1 mg to about 1000 mg of hops cone extract, preferably from about 10 mg to about 500 mg. In a preferred embodiment, the composition may comprise about 20 mg hops cone extract per serving.

The hops extract of the present invention comprises at least one substance selected from the group of humulone, xanthohumol, and myrcenol. Preferably, the hops extract comprises a combination of humulone, xanthohumol, and myrcenol. It should be noted that a dietary composition of the present may be formulated using purified humulone, xanthohumol, and/or myrcenol not in the form of hops extract or hops cone extract.

Magnolia Extract

Magnolia (Magnolia officinalis) is a tree native to China. Its bark extract has been used in traditional Chinese Medicine for its sedative and anxiolytic actions. Two major bioactive constituents of Magnolia bark extract which have been characterized are magnolol and honokiol. Both magnolol and honokiol, through their modulation of the benzodiazepine site of the GABA-A receptor, have been demonstrated, in mice, to shorten the sleep latency to non-rapid eye movement (non-REM, NREM) sleep while increasing the amount of NREM sleep. REM sleep amount remained about the same. The sedative effects of Magnolia extract have been further demonstrated in humans. In addition, both compounds also modulate the cannabinoid and adenosine systems.

The composition herein includes magnolia bark extract to improve sleep onset and sleep quality. A serving of the said composition includes from about 1 mg to about 1000 mg of magnolia, preferably from about 5 mg to about 400 mg. A preferred dosage of said composition comprises about 100 mg of magnolia.

The magnolia extract of the present invention comprises honokiol, preferably in an amount of about 2%, and magnolol, each of which is believed to be an active ingredient of the composition of the present invention. It should be noted that a dietary composition of the present may be formulated using purified honokiol and/or magnolol not in the form of magnolia extract.

Melatonin

Melatonin is a hormone produced from the amino acid tryptophan in the pineal gland of the brain in response to darkness, while light suppresses its production. Consequently, melatonin levels fluctuate throughout the day according to the light/dark cycle with a peak in the middle of the night. Melatonin's role in sleep regulation has been extensively studied. It has the ability to reduce sleep onset time and increase sleep duration. It's action on certain neural targets underlie its effect on the central clock mechanism and the sleep/wake cycle.

Low daylight, prolonged blue light exposure at night, shift work, and aging all affect melatonin production which could lead to sleep and disturbances. Exogenous melatonin can help improve sleep and normalize the internal clock. In fact, melatonin supplementation is used to treat jetlag as well as free-running rhythm disorder or hypernychthemeral syndrome. Certain plants are rich in melatonin, also called phytomelatonin.

The composition described herein may include melatonin to improve sleep onset and sleep quality. A serving of the composition of the present invention comprises from about .1 mg to about 1000 mg melatonin, preferably from about 0.5 mg to about 700 mg melatonin. A preferred dosage of the composition of the present invention comprises about 2 mg melatonin.

L-Theanine

L-theanine (N-ethyl-L-glutamine), also known as "theanine," is an amino acid abundant in tea leaves and also present in some mushrooms. Green tea (Camellia sinensis) is well known in Traditional Chinese Medicine for its sedative effect. In animal models theanine reduces markers of stress such as blood pressure. In humans, administration of theanine resulted in a reduction in heart rate and salivary immunoglobulin A (s-IgA) during an acute stress task. This ability to induce relaxation and reduce psychological stress confirmed by the production of alpha brain waves soon after ingestion, is conducive to sedation and sleep as several studies demonstrate. This effect seems to be related to the modulation of a wide range of neurotransmitters, and in particular, glutamate.

In an embodiment of the present invention the sleep composition comprises from about 10 mg to about 1000 mg of L-theanine, preferably from about 20 mg to about 600 mg L-theanine. A preferred dosage of L-theanine in the present composition comprises about 200 mg per serving.

Magnesium

Magnesium is a mineral that is important for growth and maintenance of bones. It is also important for nerves, muscles, and gastro-intestinal function. Magnesium is typically found in human and animal diets and may specifically be derived from fiber-rich plants.

Besides its crucial role in nerve cell function, magnesium is thought to modulate glutamatergic and GABAergic neurotransmission as well as counteracting angiotensin II (ATII) thus influencing the HPA system.

Since all three systems are involved in the modulation of stress and sleep, it is not surprising that studies of the effect of magnesium supplements on sleep quality and stress reduction have demonstrated encouraging results.

In an embodiment of the present invention, the sleep composition may comprise from about 1 mg to about 1000 mg magnesium, preferably from about 10 mg to about 350 mg magnesium. A preferred dosage of magnesium in the present invention comprises about 200 mg magnesium.

Rhodiola Extract

Rhodiola rosea, also known as "golden root, Arctic root," and "roseroot," is a plant originating from Europe and Asia. It has been used in traditional medicine for its adaptogenic and anti-inflammatory effects to enhance performance and reduce weakness due to fatigue and infection. An "adaptogen" is an agent conferring non-specific resistance against adverse biological, chemical, and physical stressors.

A number of compounds have been isolated from rhodiola roses roots, including fatty acids, flavonoids (e.g., ridonin, ridiolin, rhidiosin, acetylrodalgin, and tricin), tannins, polyphenols (e.g., gallic acid, chlorogenic acid, hydroxycinnamic acid), and (e.g., beta-sitosterol dukosterol).

Salidroside, tyrosol, and rosavin (or rosavine) are three major compounds showing antioxidative, cardioprotective, adaptogenic, and other therapeutic effects.

The combination of these three components found in rhodiola root extract have been investigated and demonstrated in pre-clinical and clinical studies to contribute to reducing stress and fatigue and improving mood and supporting the immune system.

In an embodiment of the present invention, the composition of the present invention comprises from about 1 mg to about 1200 mg rhodiola extract, preferably from about 20 mg to about 1000 mg rhodiola extract. A preferred dosage of rhodiola extract is about 200 mg per serving.

Spearmint Extract and/or Green Tea Extract

Spearmint extract comes from the spearmint plant, which is a plant from the Mentha genus (Lamiaceae family), which is known for improving cognitive function, mood, and sleep. The polyphenol rosmarinic acid (RA) is an antioxidant and major component of the spearmint extract. RA has demonstrated sedative activity, mediated through the GABA-A system, as observed in clinical studies in mice.

In humans, spearmint-extract rosmarinic acid in combination with ECGC improved sleep quality and daytime functioning. Pre-clinical work indicates that ECGC attenuates acute stress responses through the GABAergic system.

Green tea extract comes from the plant Camellia sinensis. Black tea, green tea, and oolong tea are all made from the same plant but prepared using different processing methods. Green tea contains polyphenols, which include the most active type epigallocatechin gallate (EGCG), which is known for reduction of stress response.

In an embodiment of the present invention, the sleep composition of the present invention comprises from about 1 mg to about 1000 mg of spearmint extract, green tea extract, and/or blends thereof, preferably from about 200 mg to about 800 mg. A preferred dosage of spearmint extract is about 485 mg per serving.

Vitamin B6

Vitamin B6, known as pyridoxine, has been shown to be helpful to those suffering from insomnia linked to a deficiency. Specifically, such deficiency often rises from renal function deficiency or malabsorption issues linked to a gastrointestinal disorder. Vitamin B6 acts at the level of the biosynthetic pathways by improving the conversion of 5-HTP into melatonin. Vitamin B6 administered in conjunction with melatonin and tryptophan, the precursor of 5-HTP or magnesium, improves sleep duration and sleep quality.

More recently, a similar amelioration of sleep status was observed in a study combining it with poly-gamma-glutamic acid.

In a preferred embodiment, the composition comprises from about 2 mg to about 100 mg of Vitamin B6, preferably from about 5 mg to about 50 mg, preferably in a water-soluble form. In a most preferred embodiment, the composition comprises about 10 mg vitamin B6.

EXAMPLES

Beverage A comprised ingredients as described herein in the following amounts, as shown by Table 1:

TABLE 1

| Ingredient | Active ingredients | Amount |
|---|---|---|
| Magnolia bark extract | 2% honokiol, magnolol | 100 mg |
| Hops extract | Humulone, xanthohumole, and myrcenol | 20 mg |
| Melatonin | | 2 mg |
| Magnesium | | 200 mg |
| Rhodiola extract | 3% rosavine, 1% salidroside | 200 mg |
| L-theanine | | 200 mg |
| Spearmint extract and green tea extract | 13.5% rosmarinic acid; ECGC | 485 mg |
| Vitamin B6 | | 10 mg |

Beverage A was formed into a "mocktail" having additional inactive ingredients to form a beverage suitable for ingestion by participants. Beverage B was a placebo composition having the same inactive ingredients to form the mocktail beverage, and without the ingredients shown in Table 1.

Participants were provided daily servings of either Beverage A or Beverage B. Sleep characteristics were tracked using headbands measuring sleep activity. Further, participants kept journals detailing sleep characteristics. The following graphs show average sleep characteristics from headband data showing significant improvement of sleep characteristics in the group that ingested Beverage A, the composition including the blend of the present invention.

FIG. 1 compares observed total sleep time over two weeks in subjects taking the Beverage A (A) and subjects taking Beverage B (B). Objective sleep parameters' statistical analysis showed that the blend in Beverage A significantly improved total sleep time compared to Beverage B (>95% confidence level).

Figure 2:
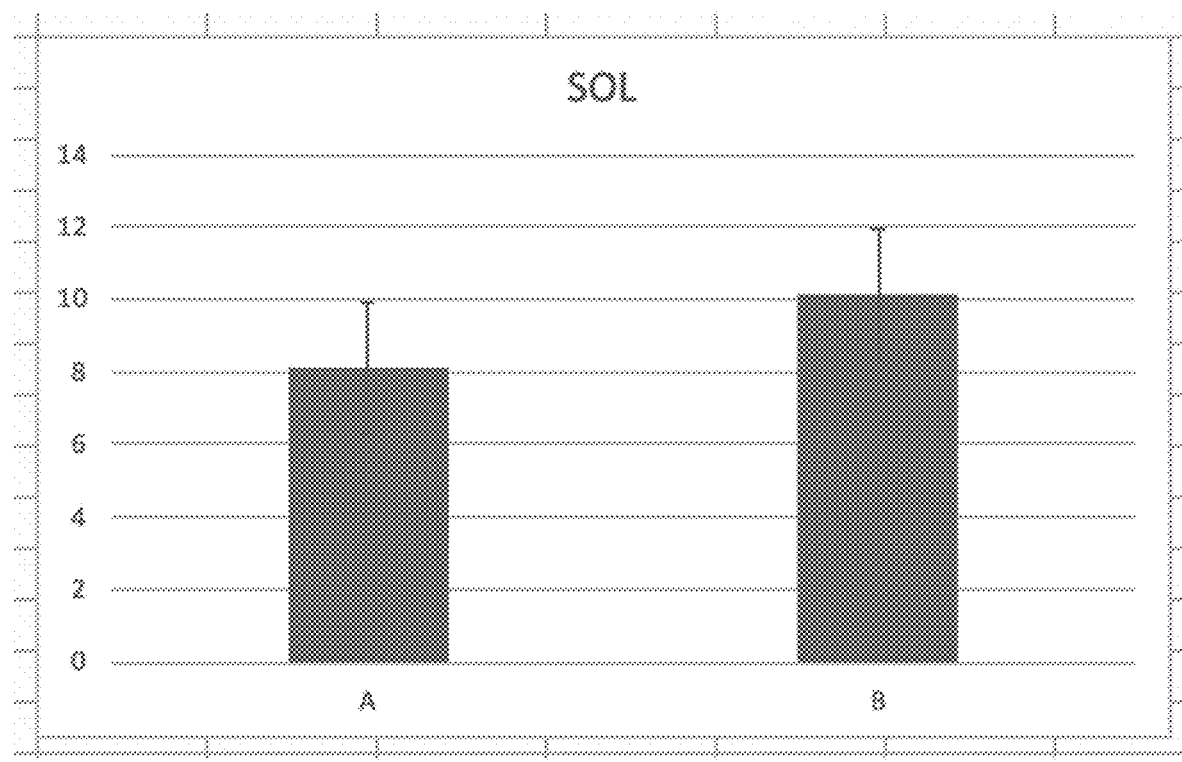
FIG. 2 illustrates a graph comparing observed sleep onset latency over two weeks in subjects taking Beverage A (A) and subjects taking Beverage B (B) in an embodiment of the present invention.

FIG. 2 compares observed sleep onset latency over two weeks in subjects taking Beverage A (A) and subjects taking Beverage B (B). Objective sleep parameters' statistical analysis showed that the blend in Beverage A significantly improved sleep onset latency compared to Beverage B (SOL) (>90% confidence level).

Figure 3:
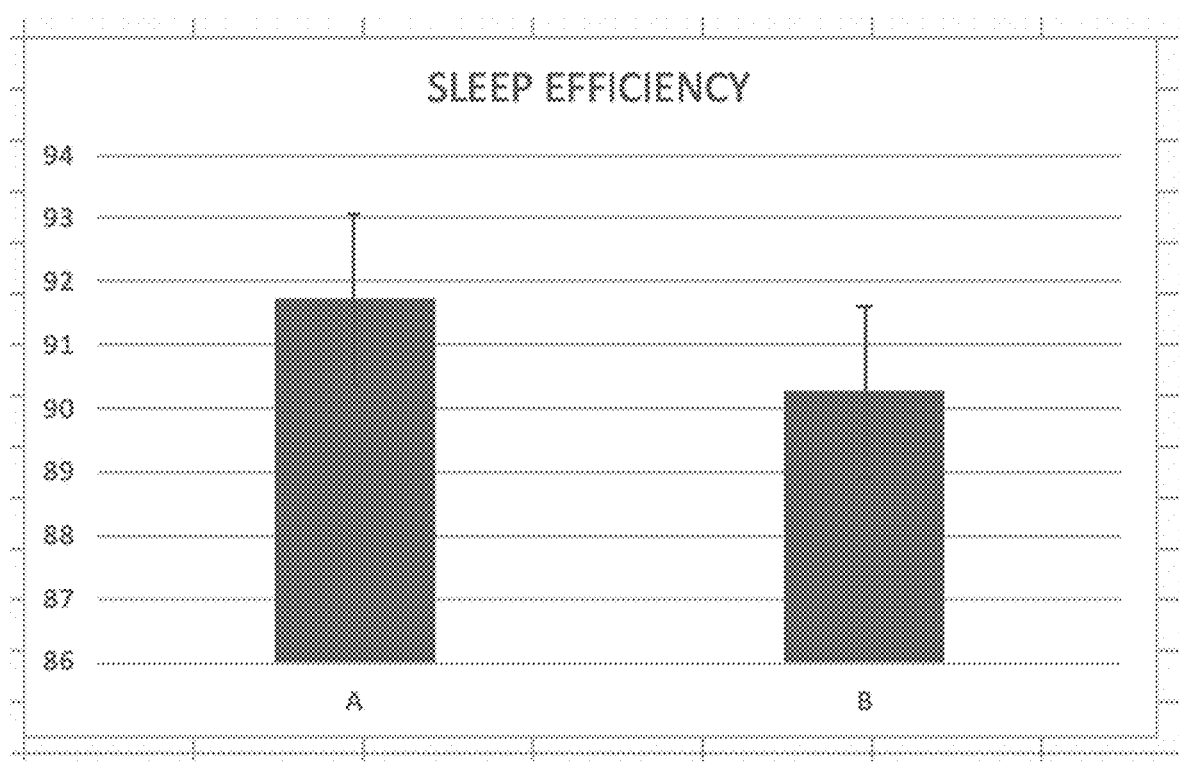
FIG. 3 illustrates a graph comparing observed sleep efficiency over two weeks in subjects taking Beverage A (A) and subjects taking Beverage B (B) in an embodiment of the present invention.

FIG. 3 compares observed sleep efficiency over two weeks in subjects taking Beverage A (A) and subjects taking Beverage B (B). Objective sleep parameters' statistical analysis showed that the blend in Beverage A significantly improved sleep efficiency compared to Beverage B (>95% confidence level).

The data above in FIGS. 1-3 represent significant synergistic effects of the blends of the present invention.

Beverage Example

In an embodiment of the present invention, a beverage example was formulated in the following amounts, as shown by Table 2:

TABLE 2

| Ingredient | Active ingredients | Percent of total beverage | Percent of total blend of active ingredients |
|---|---|---|---|
| Juice concentrate | | 2.71 | n/a |
| Citric acid | | 0.12 | n/a |
| Sugar | | 3.1 | n/a |
| Stabilizer | | 0.3 | n/a |
| Stevia | | 3.2 | n/a |
| Flavor | | 0.59 | n/a |
| Magnolia bark extract | 2% honokiol, magnolol | 0.04 | 3 |
| Hops extract | Humulone, xanthohumole, and myrcenol | 0.01 | .8 |
| Melatonin | | 0.001 | 0.08 |
| Magnesium | | 0.88 | 66 |
| Rhodiola extract | 3% rosavine, 1% salidroside | 0.09 | 6.6 |
| L-theanine | | 0.09 | 6.6 |
| Spearmint extract and green tea extract | 13.5% rosmarinic acid; ECGC | 0.21 | 16 |
| Vitamin B6 | | 0.004 | 0.3 |
| Water | | 88.651 | n/a |

The above-identified ingredients were blended together to form a Sangria-flavored beverage.

Water Modifying Powder Example

In an embodiment of the present invention, a water modifying powder example was formulated in the following amounts, as shown by Table 3:

TABLE 3

| Ingredient | Active ingredients | Percent of total powder | Percent of total blend of active ingredients |
|---|---|---|---|
| Flavor | | 15.34 | n/a |
| Citric acid | | 6.8 | n/a |
| Monk fruit 50% | | 0.09 | n/a |
| Stevia Reb A | | 0.09 | n/a |
| Erythritol | | 47.69 | n/a |
| Magnolia bark extract | 2% honokiol, magnolol | 1.00 | 3 |
| Hops extract | Humulone, xanthohumole, and myrcenol | 0.20 | 0.7 |
| Melatonin | | 0.02 | 0.07 |
| Magnesium | | 19.85 | 66 |
| Rhodiola extract | 3% rosavine, 1% salidroside | 2.00 | 6.6 |
| L-theanine | | 2.00 | 6.6 |
| Spearmint extract and green tea extract | 13.5% rosmarinic acid; ECGC | 4.84 | 16 |
| Vitamin B6 | | 0.100 | 0.3 |

The above-identified ingredients were blended together to form a powder for dispensing in an amount of water for drinking.

Gummy Example

In an embodiment of the present invention, a gummy was formulated in the following amounts, as shown by Table 4:

TABLE 4

| Ingredient | Active ingredients | Percent of total gummy | Percent of total blend of active ingredients |
|---|---|---|---|
| Water | | 20.5 | n/a |
| Pectin type D slow set | | 0.6 | n/a |
| Sucrose | | 23.69 | n/a |
| Glucose syrup 42DE | | 13.12 | n/a |
| Isofructose Syrup | | 8.42 | n/a |
| Sodium citrate 2H20 | | 0.06 | n/a |
| Gelatin 150 bloom | | 6.5 | n/a |
| Citric Acid (50% sol w/v) | | 2.5 | n/a |
| Magnolia bark extract | 2% honokiol, magnolol | 1.11 | 3 |
| Hops extract | Humulone, xanthohumole, and myrcenol | 0.22 | 0.6 |
| Melatonin | | 0.02 | .06 |
| Magnesium | | 22.00 | 66 |
| *Rhodiola* extract | 3% rosavine, 1% salidroside | 2.20 | 6.6 |
| L-theanine | | 2.20 | 6.6 |
| Spearmint extract and green tea extract | 13.5% rosmarinic acid; ECGC | 5.40 | 16 |
| Vitamin B6 | | 0.11 | 0.3 |
| (Evaporation) | | −8.66 | |

The above-identified ingredients were blended together to form a gummy for ingestion. A serving size included two gummies of approximately 9 grams each.

It should be noted that various changes and modifications to the presently preferred embodiments described herein will be apparent to those skilled in the art. Such changes and modifications may be made without departing from the spirit and scope of the present invention and without diminishing its attendant advantages. Further, references throughout the specification to "the invention" are nonlimiting, and it should be noted that claim limitations presented herein are not meant to describe the invention as a whole. Moreover, the invention illustratively disclosed herein suitably may be practiced in the absence of any element which is not specifically disclosed herein.

We claim:

1. A dietary composition formulated in a therapeutic effective amount to promote restful sleep in humans or animals consisting of a blend of:
   a first substance selected from the group consisting of humulone, xanthohumol, myrcenol, and combinations thereof;
   a second substance selected from the group consisting of honokiol, magnolol, and combinations thereof;
   a third substance selected from the group consisting of rosavine, tyrosol, salidroside, and combinations thereof;
   a fourth substance selected from the group consisting of rosmarinic acid, epigallocatechin gallate, and combinations thereof;
   melatonin;
   L-theanine;
   magnesium;
   vitamin B6 and
   optionally an excipient;
   wherein the dietary composition is in the form of a pill, a capsule, a tablet, a softgel, a lozenge, a powder, a liquid, a food, a beverage, a gummy, or an orally-dissolving film strip.

2. The dietary composition of claim 1, wherein the first substance is derived from hops.

3. The dietary composition of claim 2, wherein the first substance is in the form of hops extract.

4. The dietary composition of claim 1, wherein the third substance is derived from rhodiola.

5. The dietary composition of claim 4, wherein the third substance is in the form of rhodiola extract.

6. The dietary composition of claim 1, wherein the fourth substance is derived from an ingredient selected from the group consisting of spearmint, green tea, and a blend thereof.

7. The dietary composition of claim 6, wherein the fourth substance is in the form of an ingredient selected from the group consisting of spearmint extract, green tea extract, and a blend thereof.

8. The dietary composition of claim 1, wherein the second substance is derived from magnolia.

9. The dietary composition of claim 8, wherein the second substance is in the form of magnolia bark extract.

10. The dietary composition of claim 1, wherein the first substance is from hops extract and the hops extract is present in the blend in an amount between about 0.1% and about 70% by weight, wherein the second substance is from magnolia bark extract and the magnolia bark extract is present in the blend in an amount between about 0.1% and about 65% by weight, wherein the melatonin is present in the blend in an amount between about 0.1% and about 75% by weight, wherein the magnesium is present in the blend in an amount between about 0.1% and about 75% by weight, wherein the third substance is from rhodiola extract and the rhodiola extract is present in the blend in an amount between about 0.1% and about 80% by weight, wherein L-theanine is present in the blend in an amount between about 0.1% and about 75% by weight, wherein the fourth substance is from an ingredient selected from the group consisting of spearmint extract, green tea extract, and a combination thereof and the ingredient is present in the blend in an amount between about 0.1% and about 95% by weight, and the vitamin B6 is present in the blend in an amount between about 0.01% and about 30% by weight.

11. The dietary composition of claim 1, wherein the first substance is from hops extract and the hops extract is present in the blend in an amount between about 1% and about 20% by weight, wherein the second substance is from magnolia bark extract and the magnolia bark extract is present in the blend in an amount between about 1% and about 40% by weight, wherein the melatonin is present in the blend in an amount between about 0.1% and about 10% by weight, wherein the magnesium is present in the blend in an amount between about 1% and about 40% by weight, wherein the third substance is from rhodiola extract and the rhodiola extract is present in the blend in an amount between about 1% and about 40% by weight, wherein L-theanine is present in the blend in an amount between about 1% and about 50% by weight, wherein the fourth substance is from an ingredient selected from the group consisting of spearmint extract, green tea extract, and combinations thereof and the ingredient is present in the blend in an amount between about 1% and about 60% by weight, and the vitamin B6 is present in the blend in an amount between about 0.1% and about 10% by weight.

12. The dietary composition of claim 1, wherein the first substance is from hops extract and the hops extract is present in the dietary composition in an amount between about 10 mg and about 500 mg, wherein the second substance is from magnolia bark extract and the magnolia bark extract is present in the dietary composition in amount between about 5 mg and about 400 mg, wherein the melatonin is present in the dietary composition in an amount between about 0.5 mg and about 700 mg, wherein the magnesium is present in the dietary composition in an amount between about 10 mg and about 350 mg, wherein the third substance is from rhodiola extract and the rhodiola extract is present in the dietary composition in an amount between about 20 mg and about 1000 mg, wherein L-theanine is present in the dietary composition in an amount between about 20 mg and about 600 mg, wherein the fourth substance is from an ingredient selected from the group consisting of spearmint extract, green tea extract, and combinations thereof and the ingredient is present in the dietary composition in an amount between about 200 mg and about 800 mg, and the vitamin B6 is present in the dietary composition in an amount between about 2 mg and about 100 mg.

13. The dietary composition of claim 1, wherein the first substance is from hops extract and the hops extract is present in the dietary composition in an amount between about 15 mg and about 35 mg, wherein the second substance is from magnolia bark extract and the magnolia bark extract is present in the dietary composition in amount between about 50 mg and about 150 mg, wherein the melatonin is present in the dietary composition in an amount between about 1 mg and about 3 mg, wherein the magnesium is present in the dietary composition in an amount between about 100 mg and about 300 mg, wherein the third substance is from rhodiola extract and the rhodiola extract is present in the dietary composition in an amount between about 100 mg and about 500 mg, wherein L-theanine is present in the dietary composition in an amount between about 100 mg and about 400 mg, wherein the fourth substance is from an ingredient selected from the group consisting of spearmint extract, green tea extract, and combinations thereof and the ingredient is present in the dietary composition in an amount between about 300 mg and about 600 mg, and the vitamin B6 is present in the dietary composition in an amount between about 5 mg and about 50 mg.

14. The dietary composition of claim 1, wherein the first substance is from hops extract and the hops extract is present in the dietary composition in an amount of about 20 mg, wherein the second substance is from magnolia bark extract and the magnolia bark extract is present in the dietary composition in amount of about 100 mg, wherein the melatonin is present in the dietary composition in an amount of about 2 mg, wherein the magnesium is present in the dietary composition in an amount of about 200 mg, wherein the third substance is from rhodiola extract and the rhodiola extract is present in the dietary composition in an amount of about 200 mg, wherein L-theanine is present in the dietary composition in an amount of about 200 mg, wherein the fourth substance is from an ingredient selected from the group consisting of spearmint extract, green tea extract, and combinations thereof and the ingredient is present in the dietary composition in an amount of about 485 mg, and the vitamin B6 is present in the dietary composition in an amount of about 10 mg.

15. A method of promoting restful sleep in humans or animals comprising the steps of:
providing a dietary composition formulated in a therapeutic effective amount to promote restful sleep in humans or animals consisting of a blend of a first substance selected from the group consisting of humulone, xanthohumol, myrcenol, and combinations thereof; a second substance selected from the group consisting of honokiol, magnolol, and combinations thereof; a third substance selected from the group consisting of rosavine, tyrosol, salidroside, and combinations thereof; a fourth substance selected from the group consisting of rosmarinic acid, epigallocatechin gallate, and combinations thereof; melatonin; L-theanine; magnesium; vitamin B6; and an optional excipient and
forming the dietary composition into an ingestible form wherein the ingestible form is a pill, a capsule, a tablet, a softgel, a lozenge, a powder, a liquid, a food, a beverage, a gummy, or an orally-dissolving film strip.

16. The method of claim 15, wherein the first substance is from hops extract, the second substance is from magnolia bark extract, the third substance is from rhodiola extract, and the fourth substance is from an ingredient selected from the group consisting of spearmint extract, green tea extract, and a combination thereof.

17. The method of claim 16, wherein the hops extract is present in the blend in an amount between about 0.1% and about 70% by weight, the magnolia bark extract is present in the blend in an amount between about 0.1% and about 65% by weight, wherein the melatonin is present in the blend in an amount between about 0.1% and about 75% by weight, wherein the magnesium is present in the blend in an amount between about 0.1% and about 75% by weight, wherein the rhodiola extract is present in the blend in an amount between about 0.1% and about 80% by weight, wherein L-theanine is present in the blend in an amount between about 0.1% and about 75% by weight, wherein the ingredient selected from the group consisting of spearmint extract, green tea extract, and a combination thereof is present in the blend in an amount between about 0.1% and about 95% by weight, and the vitamin B6 is present in the blend in an amount between about 0.01% and about 30% by weight.

18. The method of claim 16, wherein the hops extract is present in the dietary composition in an amount between about 10 mg and about 500 mg, wherein the magnolia extract is present in the dietary composition in an amount between about 5 mg and about 400 mg, wherein the melatonin is present in the dietary composition in an amount between about 0.5 mg and about 700 mg, wherein the magnesium is present in the dietary composition in an amount between about 10 mg and about 350 mg, wherein the third substance is from rhodiola extract and the rhodiola extract is present in the dietary composition in an amount between about 20 mg and about 1000 mg, wherein L-theanine is present in the dietary composition in an amount between about 20 mg and about 600 mg, wherein the ingredient selected from the group consisting of spearmint extract, green tea extract, and a combination thereof is present in an amount between about 200 mg and about 800 mg, and the vitamin B6 is present in the dietary composition in an amount between about 2 mg and about 100 mg.

* * * * *